(12) United States Patent
Kohara et al.

(10) Patent No.: US 11,123,024 B2
(45) Date of Patent: Sep. 21, 2021

(54) X-RAY CT DEVICE AND IMAGE DISPLAY METHOD FOR PARALLEL IMAGING PROCESS AND RECONSTRUCTION PROCESS BASED ON DATA-PRESERVATION PROCESS

(71) Applicant: Hitachi, Ltd., Tokyo (JP)

(72) Inventors: Ryota Kohara, Tokyo (JP); Tsuyoshi Suzuki, Tokyo (JP); Yuta Ogura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 23 days.

(21) Appl. No.: 16/471,527

(22) PCT Filed: Dec. 5, 2017

(86) PCT No.: PCT/JP2017/043691
§ 371 (c)(1),
(2) Date: Jun. 19, 2019

(87) PCT Pub. No.: WO2018/159051
PCT Pub. Date: Sep. 7, 2018

(65) Prior Publication Data
US 2019/0383755 A1 Dec. 19, 2019

(30) Foreign Application Priority Data
Mar. 1, 2017 (JP) ............................. JP2017-038596

(51) Int. Cl.
*A61B 6/03* (2006.01)
*G01N 23/046* (2018.01)
(Continued)

(52) U.S. Cl.
CPC .............. *A61B 6/032* (2013.01); *A61B 6/035* (2013.01); *A61B 6/44* (2013.01); *A61B 6/4429* (2013.01);
(Continued)

(58) Field of Classification Search
CPC ........... A61B 6/032; A61B 6/035; A61B 6/44; A61B 6/4429; A61B 6/4435;
(Continued)

(56) References Cited

U.S. PATENT DOCUMENTS

| 5,513,237 A | 4/1996 | Nobuta et al. |
| 5,699,399 A | 12/1997 | Ozaki |

(Continued)

FOREIGN PATENT DOCUMENTS

| JP | H07-194592 A | 8/1995 |
| JP | H0824252 A | 1/1996 |

(Continued)

OTHER PUBLICATIONS

An English translation of JP H07-194592 A by Patent Translate.*
(Continued)

*Primary Examiner* — Allen C. Ho
(74) *Attorney, Agent, or Firm* — Baker Botts L.L.P.

(57) ABSTRACT

Arrangement to reduce a time until a first image is displayed, to reduce a standby time until the next imaging is started, and to uniformize a time interval in a case where a plurality of images are displayed. An X-ray CT device detects a dose of an X-ray, a storage unit that preserves image data, a calculation unit that generates, as the image data, projection data on the basis of the X-ray data in parallel to an imaging process in the scanner, preserves the projection data, notifies a display control unit of preservation information, performs a reconstruction process, a display unit that displays an image generated per the X-ray data, and the display control unit that controls a display timing of a reconstructed image to be displayed on the display unit on the basis of the preservation information and the reconstruction information.

7 Claims, 9 Drawing Sheets

(51) Int. Cl.
*G06T 11/00* (2006.01)
*A61B 6/00* (2006.01)

(52) U.S. Cl.
CPC .......... *A61B 6/4435* (2013.01); *A61B 6/4441* (2013.01); *A61B 6/4447* (2013.01); *A61B 6/46* (2013.01); *A61B 6/461* (2013.01); *A61B 6/463* (2013.01); *A61B 6/482* (2013.01); *A61B 6/486* (2013.01); *A61B 6/487* (2013.01); *A61B 6/52* (2013.01); *A61B 6/5205* (2013.01); *A61B 6/5211* (2013.01); *A61B 6/54* (2013.01); *A61B 6/542* (2013.01); *A61B 6/545* (2013.01); *G01N 23/046* (2013.01); *G06T 11/003* (2013.01); *G01N 2223/401* (2013.01); *G01N 2223/408* (2013.01); *G01N 2223/419* (2013.01); *G06T 2210/41* (2013.01)

(58) Field of Classification Search
CPC ....... A61B 6/4441; A61B 6/4447; A61B 6/46; A61B 6/461; A61B 6/463; A61B 6/486; A61B 6/487; A61B 6/482; A61B 6/52; A61B 6/5205; A61B 6/5211; A61B 6/54; A61B 6/542; A61B 6/545
USPC ..... 378/4, 5, 16, 19, 42, 62, 91, 98.9, 98.11, 378/196–198, 210, 901
See application file for complete search history.

(56) References Cited

U.S. PATENT DOCUMENTS

| | | | | |
|---|---|---|---|---|
| 7,245,691 B2* | 7/2007 | Kiyono | ............... | A61B 6/032 378/4 |
| 8,208,600 B2* | 6/2012 | Tsumuraya | ............ | H01J 35/06 378/9 |
| 9,339,249 B2* | 5/2016 | Fujisawa | ............... | A61B 6/488 |
| 9,538,972 B2* | 1/2017 | Mukumoto | ............. | A61B 6/52 |
| 9,597,051 B2* | 3/2017 | Gatayama | ............... | A61B 6/54 |
| 9,721,361 B2* | 8/2017 | Pal | ...................... | A61B 6/5258 |
| 9,980,694 B2* | 5/2018 | Takahashi | ............. | G06T 7/0012 |
| 10,019,798 B2* | 7/2018 | Ninomiya | ............... | A61B 6/03 |
| 10,101,284 B2* | 10/2018 | Koike | ................... | A61B 6/032 |
| 2010/0183117 A1 | 7/2010 | Tsumuraya et al. | | |

FOREIGN PATENT DOCUMENTS

| | | |
|---|---|---|
| JP | H08196533 A | 8/1996 |
| JP | 2001017423 A | 1/2001 |
| JP | 3512874 B2 | 3/2004 |
| JP | WO2009011422 A1 | 9/2010 |

OTHER PUBLICATIONS

International Search Report and Written Opinion for the International Patent Application No. PCT/JP2017/043691, dated Mar. 6, 2018, 8 pages.

International Preliminary Report on Patentability, dated Sep. 12, 2019, which issued during the prosecution of International Application No. PCT/JP2017/043691, which corresponds to the present application.

Office Action, dated Apr. 21, 2020, which issued during the prosecution of Japanese Application No. 2017-038596, which corresponds to the present application (English translation attached).

* cited by examiner

X-RAY CT DEVICE AND IMAGE DISPLAY METHOD FOR PARALLEL IMAGING PROCESS AND RECONSTRUCTION PROCESS BASED ON DATA-PRESERVATION PROCESS

CROSS-REFERENCE TO RELATED APPLICATIONS

This application is a national phase claiming the benefit of and priority to International Patent Application No. PCT/JP2017/043691, entitled "X-RAY CT DEVICE AND IMAGE DISPLAY METHOD", filed Dec. 5, 2017, which claims priority to Japanese Patent Application No. 2017-038596, filed Mar. 1, 2017, which are hereby incorporated by reference in their entireties.

TECHNICAL FIELD

The present invention relates to an X-ray CT device and an image display method, and particularly to an X-ray CT device which performs consecutive imaging and sequentially displays captured images, and an image display method.

BACKGROUND ART

There is an X-ray CT device which applies X-rays while rotating an X-ray tube about a subject, reconstructs projection data obtained by detecting X-rays transmitted through the subject with a detector, and thus acquires a reconstructed image of the inside of the subject. In the X-ray CT device, processes such as imaging (scanning), image reconstruction, and image display are performed in a time series. In other words, in the X-ray CT device, predetermined processing is performed on data acquired while rotating the X-ray tube and the X-ray detector, the data is temporarily stored in a storage device, image reconstruction is performed by reading the stored data, and a reconstructed image is sequentially displayed on a display device.

For example, PTL 1 discloses an X-ray CT device which repeatedly performs image reconstruction, image display, and storing of image data whenever data corresponding to a sheet is collected after imaging is started.

CITATION LIST

Patent Literature

[PTL 1] Japanese Patent No. 3512874

SUMMARY OF INVENTION

Technical Problem

However, in the X-ray CT device disclosed in PTL 1, since raw data corresponding to a single image is collected, and then a reconstruction process on the image or data preservation is started, the time is required until a first image is displayed from starting of imaging. As a result, after consecutive imaging is finished, the time is required for a reconstruction process, image display, and data preservation, and thus a standby time occurs until the next imaging is started.

In a case where consecutive imaging is performed, and a captured image is sequentially displayed, when there is a variation in an image display interval, images cannot be smoothly viewed.

The present invention has been made in light of the circumstances, and an object thereof is to reduce a time until a first image is displayed from starting of imaging, to reduce a standby time until the next imaging is started after imaging is finished, and to uniformize a time interval in a case where a plurality of images are displayed.

Solution to Problem

In order to achieve the object, the present invention provides the following means.

According to an aspect of the present invention, there is provided an X-ray CT device including a scanner that detects a dose of an X-ray which is applied from the periphery of a subject on a bed and is transmitted through the subject, and acquires X-ray data; a calculation unit that performs predetermined calculation on the X-ray data acquired by the scanner; a storage unit that preserves at least one of the X-ray data and image data which is generated on the basis of the X-ray data by the calculation unit; a display unit that displays an image generated on the basis of the X-ray data; and a display control unit that controls an image to be displayed on the display unit, in which the calculation unit includes a projection data generation unit that generates, as the image data, projection data on the basis of the X-ray data, a data preservation processing unit that preserves at least one of the X-ray data and the projection data in the storage unit in the unit of a predetermined data amount in parallel to an imaging process in the scanner, and also notifies the display control unit of preservation information indicating a progress situation of a preservation process whenever preservation of the predetermined data amount is completed, and a reconstruction processing unit that performs a reconstruction process on the projection data in the unit of a predetermined data amount so as to generate a reconstructed image in parallel to the imaging process in the scanner, and also notifies the display control unit of reconstruction information indicating a progress situation of the reconstruction process whenever the reconstruction process is performed, and in which the display control unit controls a display timing of a reconstructed image to be displayed on the display unit on the basis of the preservation information and the reconstruction information.

Advantageous Effects of Invention

According to the present invention, it is possible to reduce a time until a first image is displayed from starting of imaging, to reduce a standby time until the next imaging is started after imaging is finished, and to uniformize a time interval in a case where a plurality of images are displayed.

DESCRIPTION OF EMBODIMENTS

An X-ray CT device according to an embodiment of the present invention includes a scanner that detects a dose of an X-ray which is applied from the periphery of a subject on a bed and is transmitted through the subject, and acquires X-ray data; a calculation unit that performs predetermined calculation on the X-ray data acquired by the scanner; a storage unit that preserves at least one of the X-ray data and image data which is generated on the basis of the X-ray data by the calculation unit; a display unit that displays an image generated on the basis of the X-ray data; and a display control unit that controls an image to be displayed on the display unit, in which the calculation unit includes a projection data generation unit that generates, as the image data, projection data on the basis of the X-ray data, a data preservation processing unit that preserves at least one of the X-ray data and the projection data in the storage unit in the unit of a predetermined data amount in parallel to an imaging process in the scanner, and also notifies the display control unit of preservation information indicating a progress situation of a preservation process whenever preservation of the predetermined data amount is completed, and a reconstruction processing unit that performs a reconstruction process on the projection data in the unit of a predetermined data amount in parallel to the imaging process in the scanner, and also notifies the display control unit of reconstruction information indicating a progress situation of the reconstruction process whenever the reconstruction process is performed, and in which the display control unit controls a display timing of a reconstructed image to be displayed on the display unit on the basis of the preservation information and the reconstruction information.

According to the X-ray CT device, a reconstruction process and a projection data preservation process are performed in parallel to an imaging process, and thus it is possible to reduce the time required to display a first image from starting of imaging. Display control is performed according to preservation information and reconstruction information even though a reconstruction process and a preservation process which are sequentially performed are asynchronous, and thus it is possible to display sequentially generated reconstructed images at a uniform time interval and thus to improve operability. Preservation is also sequentially performed, and thus it is possible to reduce a standby time until the next imaging is started from finishing of imaging.

First Embodiment

Figure 1:
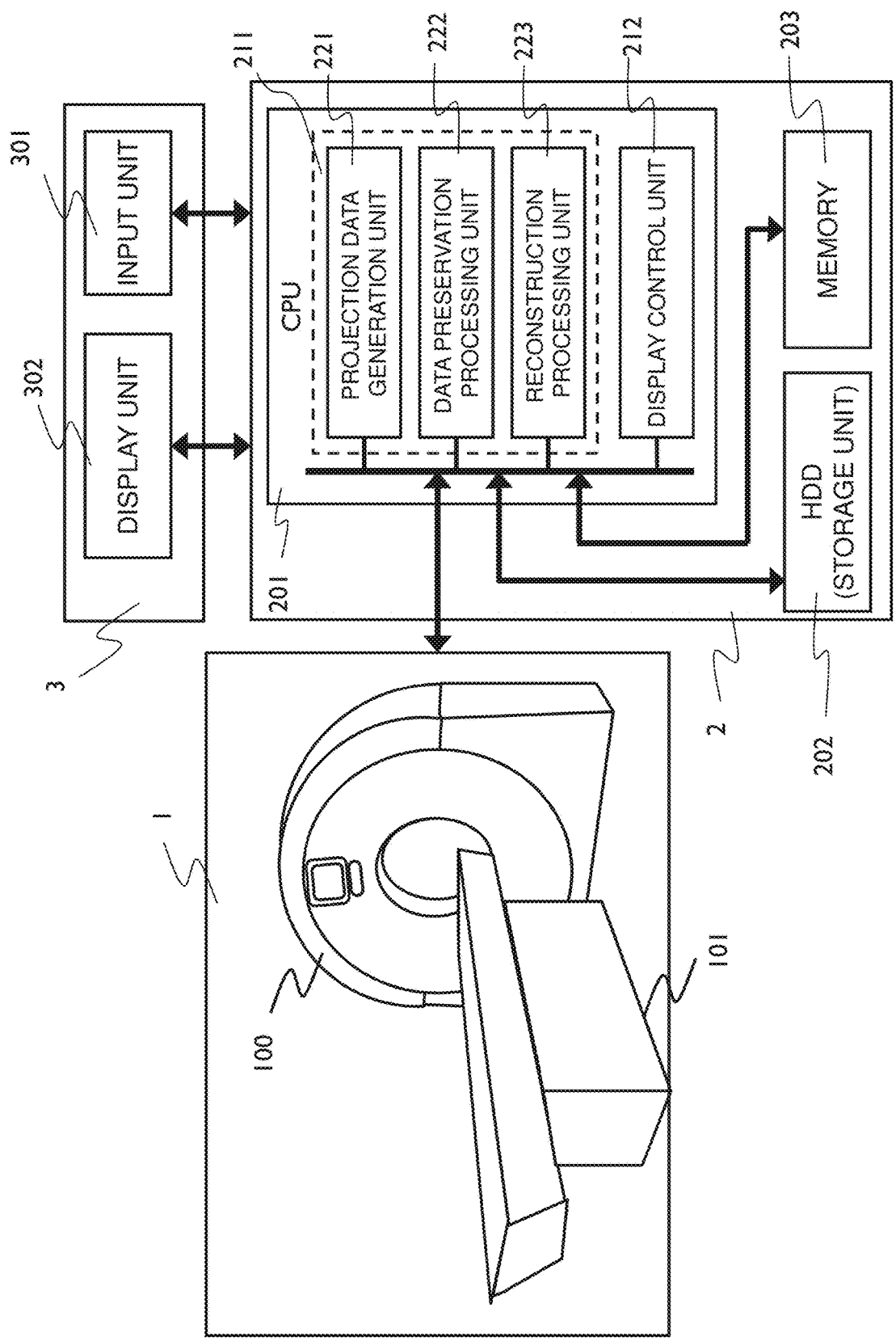
FIG. 1 is a block diagram illustrating a schematic configuration of an X-ray CT device according to a first embodiment of the present invention.

Hereinafter, an X-ray CT device according to a first embodiment of the present invention will be described with reference to the drawings. FIG. 1 illustrates the whole configuration of an X-ray CT device of the present invention. The X-ray CT device includes a scanner 1 which acquires X-ray data of a subject, a control section 2 which performs predetermined calculation on X-ray data obtained by the scanner 1, and an input/output unit 3.

The scanner 1 includes an X-ray source and an X-ray detector (not illustrated) mounted in a gantry 100, and detects a dose of X-rays which are applied from the X-ray source circulating around a subject on a bed 101 and are transmitted through the subject, so as to acquire X-ray data.

The control section 2 includes a CPU 201 which drives and controls an operation of the scanner 1, and performs predetermined calculation on X-ray data obtained from the scanner 1, and a storage unit 202 which stores data required for imaging, such as a program or a device parameter, or projection data generated by a projection data generation unit (which will be described later), and a memory 203 which stores X-ray data or projection data as image data.

The CPU 201 functions as a calculation unit 211 and a display control unit 212. Each of the units may be realized in software by reading a program stored in advance in a storage unit such as the storage unit 202 and executing the program. Some or all operations performed by each unit may be realized by an application specific integrated circuit (ASIC) or a field programmable gate array (FPGA).

The calculation unit 211 performs predetermined calculation on X-ray data acquired by the scanner 1, and generates image data including projection data or a reconstructed image on the basis of the X-ray data, and, more specifically, functions as a projection data generation unit 221, a data preservation processing unit 222, and a reconstruction processing unit 223.

The projection data generation unit 221 generates, as image data, projection data on the basis of X-ray data. More specifically, a logarithmic conversion coefficient is sequentially multiplied to X-ray data which is input from the scanner 1 and is temporarily stored in the memory 203 such that a logarithm is obtained, and thus projection data is sequentially generated to be stored in the memory 203.

The data preservation processing unit 222 preserves at least one of X-ray data or projection data in the unit of a predetermined data amount in the storage unit 202 in parallel to an imaging process in the scanner 1, and notifies the display control unit 212 of preservation information indicating a progress situation of a preservation process whenever preservation in the unit of the predetermined data amount is completed. Here, the predetermined data amount is, for example, the minimum data amount of projection data or X-ray data required to start a reconstruction process in the reconstruction processing unit 223. The data preservation processing unit 222 may use an angle number of the preserved projection data or X-ray data as preservation information.

The reconstruction processing unit 223 sequentially reads projection data generated by the projection data generation unit 221 from the memory 203, sequentially performs an inverse projection process by applying a frequency filter to the projection data such that a reconstruction process is performed on a plurality of images on the basis of the projection data, and outputs reconstructed images which are generated in an order in which the reconstruction process is finished, to the display control unit 212. In this case, the reconstruction processing unit 223 also outputs reconstruction information indicating a progress situation of the reconstruction process along with the reconstructed images.

Here, in the present embodiment, the reconstruction processing unit 223 sequentially outputs the generated reconstructed images to the display control unit 212, and thus image numbers of the generated reconstructed images correspond to reconstruction information indicating a progress situation of the reconstruction process. Therefore, the display control unit 212 is notified of an image number as reconstruction information whenever the reconstruction process is performed.

The display control unit 212 controls a reconstruction image to be displayed on a display unit 302 which will be described later on the basis of the preservation information and the reconstruction information. In the X-ray CT device according to the present embodiment, an image data preservation process and a reconstruction process are performed by the control section 2 in parallel to an imaging process in the scanner 1. Since the display control unit 212 acquires preservation information and reconstruction information, and thus recognizes progress situations of both of the preservation process and the reconstruction process, a time interval is uniformized in a case where an image is displayed, by setting a display timing of a reconstructed image even though the preservation process and the reconstruction process are not synchronized with each other instead of merely displaying the images in accordance with a generation timing of the reconstructed image. A specific process in the display control unit 212 will be described later.

The input/output unit 3 includes an input unit 301 used for a user to input imaging conditions or the like, and the display unit 302 displaying image data. As the input unit 301, a pointing device such as a mouse, a keyboard, or the like may be used. The display unit 302 displays a reconstructed image under the control of the display control unit 212. A liquid crystal monitor or the like may be used as the display unit 302. A touch panel may be used as the display unit 302, and may thus also be used as the input unit 301.

Figure 2:
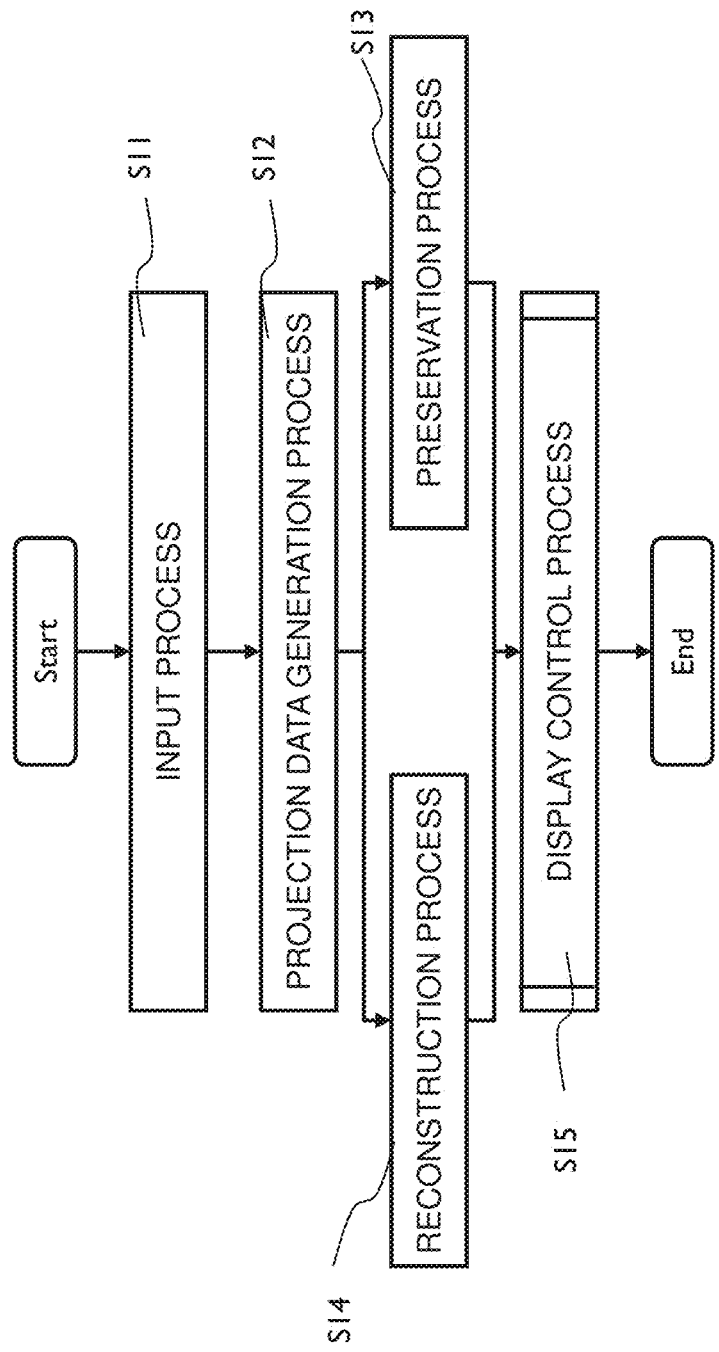
FIG. 2 is a flowchart illustrating a flow of a process until a reconstructed image is generated from imaging in the X-ray CT device according to the first embodiment of the present invention.

Next, in the X-ray CT device, with reference to a flowchart of FIG. 2, a description will be made of processes until a reconstructed image is generated from imaging.

In step S11, a process of inputting X-ray data is performed. In other words, in a case where an imaging process is performed by the scanner 1, X-ray data collected in the scanner 1 is sequentially input to the memory 203 (refer to FIG. 3). In the subsequent step S12, the projection data generation unit 221 generates projection data on the basis of the X-ray data input to the memory 203.

Figure 3:
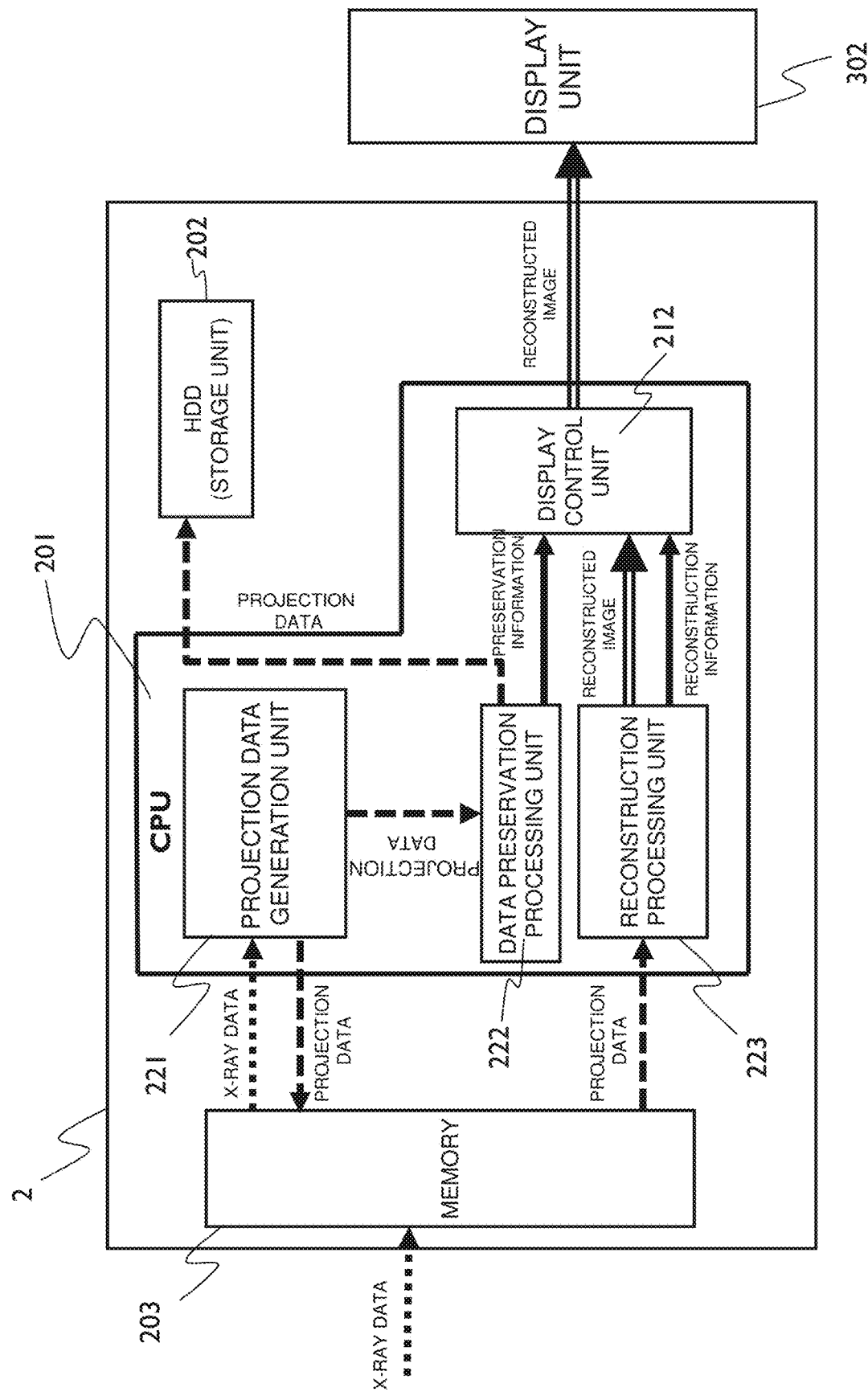
FIG. 3 is an explanatory diagram illustrating a flow of data until a reconstructed image is generated from imaging in the X-ray CT device according to the first embodiment of the present invention.

Specifically, as illustrated in FIG. 3, the projection data generation unit 221 reads the X-ray data stored in the memory 203, multiplies the X-ray data by a logarithmic conversion coefficient so as to obtain a logarithm, and performs a calibration process so as to generate projection data. In this case, a down-sampling process may be performed in an angular direction, and a noise reduction filter may be applied in the angular direction. This projection data generation process is sequentially performed whenever X-ray data is input to the memory 203. The projection data generation unit 221 stores the generated projection data into the memory 203, and also outputs the projection data to the data preservation processing unit 222.

In step S13, the data preservation processing unit 222 sequentially stores the projection data generated in step S12 into the storage unit 202, and also generates preservation information which is then output to the display control unit 212. In other words, the projection data generated by the projection data generation unit 221 is preserved into the storage unit 202 in the unit of a predetermined data amount. Here, the predetermined data amount according to the present embodiment is the minimum data amount of projection data required for the reconstruction processing unit 223 to start a reconstruction process.

The data preservation processing unit 222 counts angle numbers of preserved projection data as the preservation information, holds the latest angle number ($E_c$), and notifies the display control unit 212 of the angle number. The data preservation processing unit 222 updates the angle number ($E_c$) as the preservation information whenever the projection data preservation process is performed.

In step S14, the reconstruction processing unit 223 performs a reconstruction process on the projection data which is generated by the projection data generation unit 221 and is stored in the memory 203, in parallel to the process in step S13. In other words, the reconstruction processing unit 223 reads, from the memory 203, projection data at a plurality of angles required to perform a reconstruction process, that is, projection data which is convertible, and performs the reconstruction process thereon.

More specifically, the reconstruction processing unit 223 converts linear irradiation projection data into parallel irradiation projection data, and performs Fourier transform on the parallel irradiation projection data so as to generate frequency-domain parallel irradiation projection data. Next, the frequency-domain parallel irradiation projection data is multiplied by a frequency-domain filter such that frequency-domain filter parallel irradiation projection data is created, and inverse Fourier transform is performed on the frequency-domain filter parallel irradiation projection data such that filter parallel irradiation projection data is created.

The projection data filtering process can be performed at a high speed by using fast Fourier transform (FFT) and inverse fast Fourier transform (IFFT) as the Fourier transform and the inverse Fourier transform. A normalized Ramp filter or the like is used as the frequency-domain filter.

The reconstruction processing unit 223 calculates a coordinate of a detection element located at an intersection between a straight line passing through a focal point of an X-ray generation device and the center of a target pixel at each rotation angle of the scanner, and an X-ray detection device, and adds a projection value of filter parallel irradiation projection data corresponding to the calculated detection element position to the target pixel. The reconstruction processing unit 223 performs the same process on all pixels, so as to create a reconstructed image. As illustrated in FIG. 3, the reconstruction processing unit 223 sequentially outputs generated reconstructed images to the display control unit 212, and sequentially outputs image numbers of the generated reconstructed images to the display control unit 212 as reconstruction information.

The preservation process in step S13 and the reconstruction process in step S14 are performed in parallel to each other but are asynchronously performed. Thus, in a case where the reconstruction process is earlier than the preservation process, a reconstructed image generated by using projection data which is not preserved in the storage unit 202 may be displayed on the display unit 302. Regarding a displayed reconstructed image, it is necessary to generate a reconstructed image under reconstruction conditions which are different from those during imaging by using preserved projection data after imaging. In a case where the preservation process is required to be immediately stopped due to a user immediately stopping imaging, and the preservation process is earlier than a display process, the request cannot be ensured. Thus, in step S15, the display control unit 212 controls only a reconstructed image created by using preserved projection data to be displayed, and sequentially reconstructed images on the display unit 302 at a uniform time interval.

Figure 4:
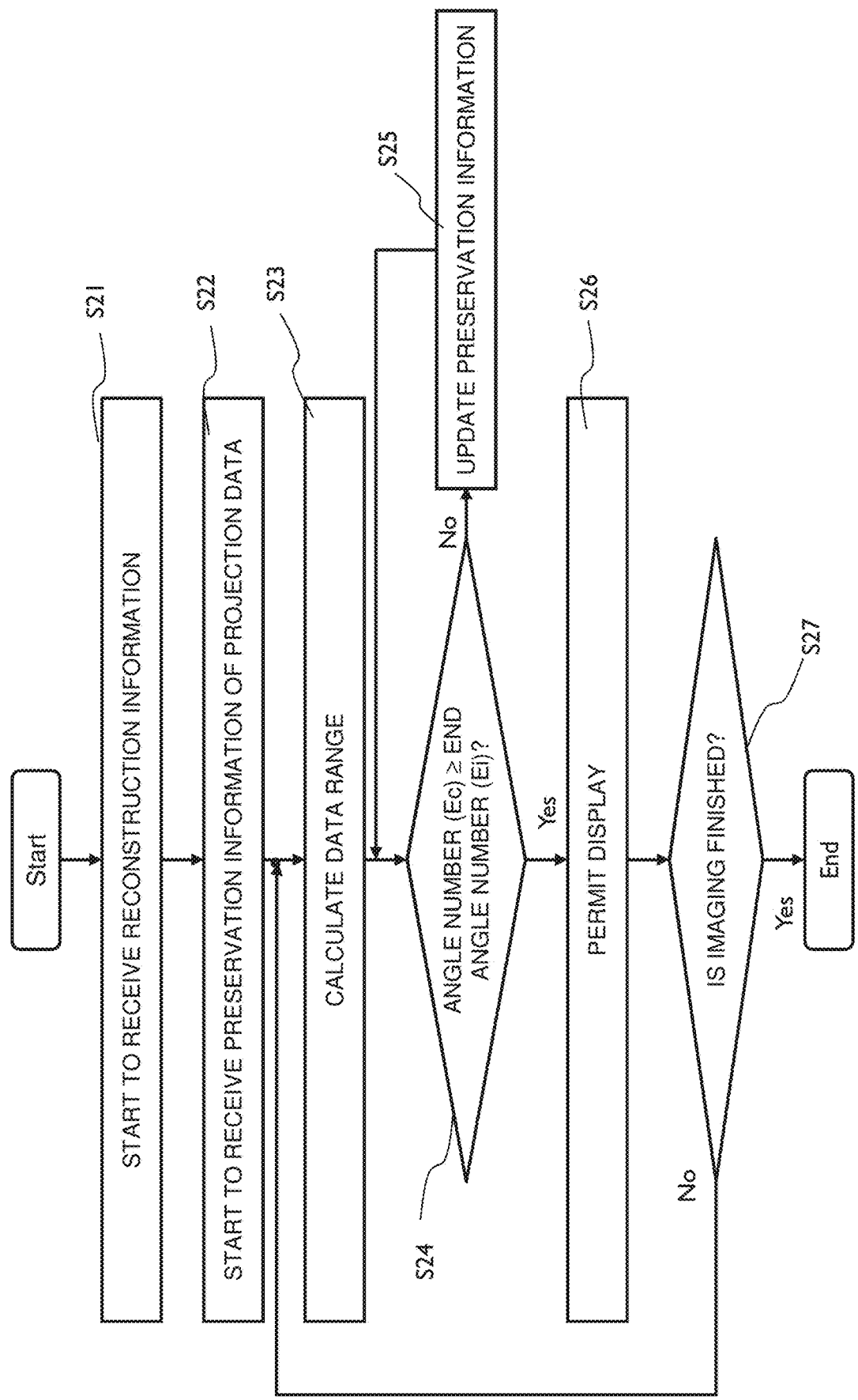
FIG. 4 is a flowchart illustrating a flow of a process in a display control unit of the X-ray CT device according to the first embodiment of the present invention.

Next, with reference to a flowchart of FIG. 4, a description will be made of details of a process in the display control unit 212.

In the X-ray CT device, in a case where imaging is started, and the control section 2 receives X-ray data from the scanner 1, and starts various processes, the display control unit 212 starts to receive reconstruction information from the reconstruction processing unit 223 in step S21. In a case where the reconstruction information starts to be received, the display control unit 212 checks an image number (i) on the basis of the reconstruction information. In other words, the display control unit 212 checks the image number (i) indicated by the reconstruction information, or checks the image number (i) by counting the number of images from which reconstructed images are generated in the reconstruction process. The image number is a positive integer starting from 1.

Next, the display control unit 212 starts to receive preservation information from the data preservation processing unit 222 in step S22. In a case where the preservation information starts to be received, the display control unit 212 checks the latest angle number (Ec) of projection data stored in the storage unit 202 on the basis of the preservation information.

In step S23, the display control unit 212 calculates a start angle number ($S_i$) and an end angle number ($E_i$) of projection data from which the reconstructed image is generated by using the image number (i) checked in step S21.

First, the number of rotations ($R_i$) is calculated on the basis of the image number (i) according to the following Equation (1). In this case, a leading image position, an image interval, a movement amount of the bed per rotation, a leading position of the bed, and a half range of an angular range required to create a single image are used.

$$R_i = (Z_0 - (Z_1 + Z_2) + (L_h + \lambda) + D \times (i-1))/L_R \quad (1)$$

Next, a center angle number ($T_i$) corresponding to the center of an angular range required to create a reconstructed image is calculated according to the following Equation (2) on the basis of the number of rotations obtained by using Equation (1).

$$T_i = CEIL((T_f + \tau) \times R_i - \delta) - (T_h + \tau/2) - 1 \quad (2)$$

The start angle number ($S_i$) and the end angle number ($E_i$) are calculated on the basis of the center angle number and a use angle number of the reconstructed image. In this case, as the use angle number, each of a front use angular range traced back from the center angle number with respect to a rotation direction and a use angular range advancing in the rotation direction is taken into consideration.

A front side angle number is referred to as a front angle number, and a rear side angle number is referred to as a rear angle number. In a case where a front angle number is traced back from a start point of a usable angular range, the front angle number is set to a usable start angle number. In a case where a rear number exceeds an end point of the usable angular range, the rear number is set to a usable end angle number. However, a use angular range of the image differs depending on an inverse projection processing method.

Here, in the respective equations, $T_f$ indicates an angular range required to create a single image, $T_h$ indicates a half range of the angular range required to create a single image, $Z_0$ indicates a leading image position, $Z_1$ indicates a leading position of the bed, $Z_2$ indicates an offset value of a bed position, $L_h$ indicates a value of a bed movement amount into which $T_h$ is converted, D indicates an image interval, i indicates an image number, $L_R$ indicates a bed movement amount per rotation, δ indicates a value for adjusting round-up, λ indicates a value of a bed movement amount into which τ/2 is converted, τ indicates an extended range of an angular range changed depending on an algorithm for an inverse projection process and required to create a single image, and CEIL indicates a round-up function.

In the next step S24, the angle number ($E_c$) related to the preservation information acquired from the data preservation processing unit 222 is compared with the end angle number ($E_i$) calculated in step S23 in terms of the magnitude. In a case where the preserved angle number is smaller than the end angle number, the image with the image number (i) is not permitted to be displayed, and the flow proceeds to step S25. In a case where the preservation information is updated, the flow returns to step S24, and the angle number ($E_c$) related to the preservation information is compared with the end angle number ($E_i$) calculated in step S23 in terms of the magnitude again.

In a case where the angle number is larger than or the same as the end angle number, the flow proceeds to step S26, the display control unit 212 permits the reconstructed image with the image number (i) to be displayed on the display unit 302, and the flow proceeds to step S27. In step S27, it is determined whether or not the overall imaging is finished, and, in a case where imaging is not finished, the flow returns to step S23, and the processes are repeatedly performed until imaging is finished. In a case where imaging is finished, the processes are finished.

Figure 5:
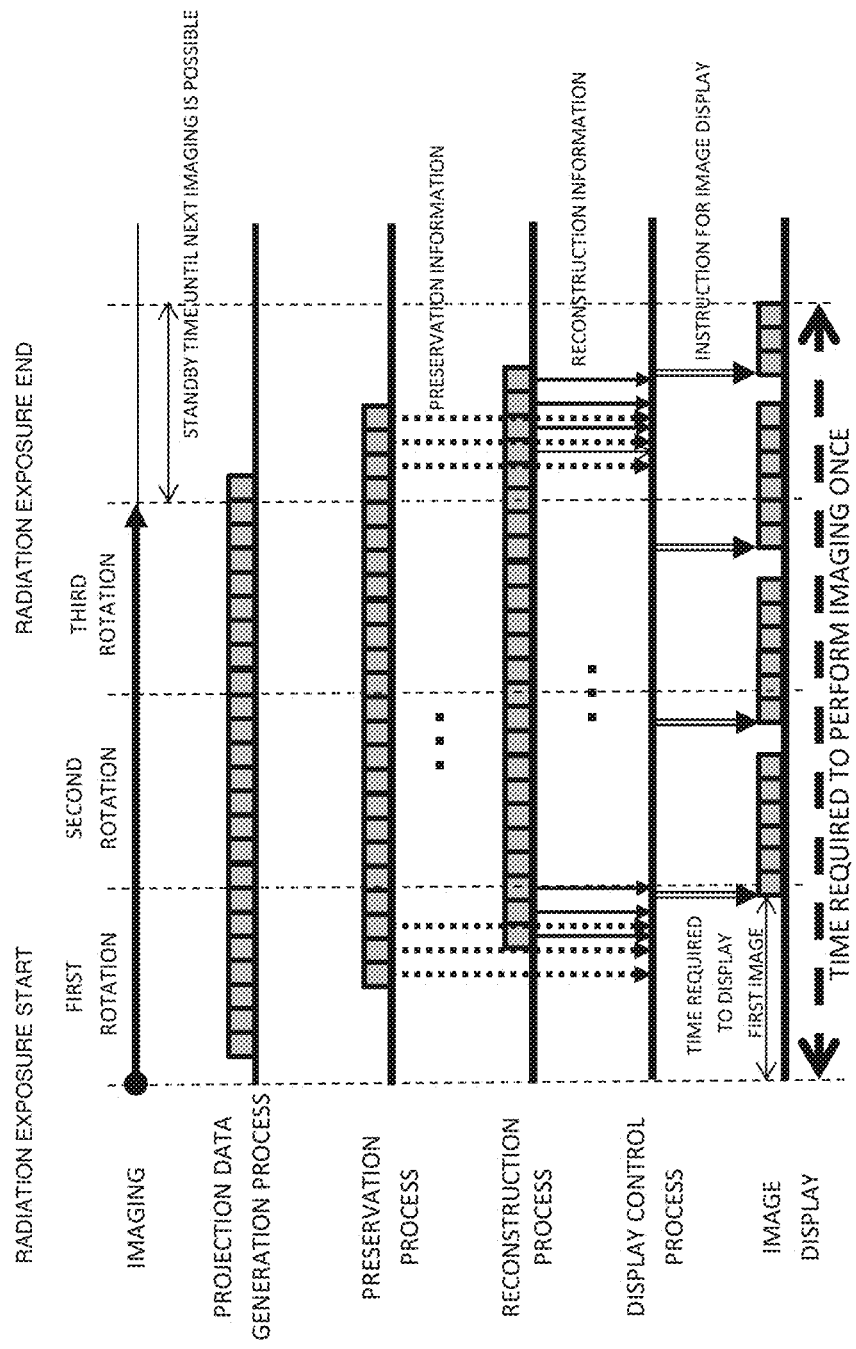
FIG. 5 is a timing chart related to display control in the X-ray CT device according to the first embodiment of the present invention.

FIG. 5 is a timing chart for each process in the X-ray CT device according to the present embodiment.

As illustrated in FIG. 5, projection data is generated and preserved for each projection data process, and thus the display control unit 212 sequentially receives preservation information. Similarly, a reconstructed image is generated for each reconstruction process, and thus the display control unit 212 sequentially receives reconstruction information. As illustrated in FIG. 5, the display control unit 212 sets a timing such that a reconstructed image is displayed after preservation of projection data from which the reconstructed image is generated is completed on the basis of the preservation information and the reconstruction information, in a case where the reconstructed image is displayed, and thus uniformizes a time interval of image display.

Figure 6:
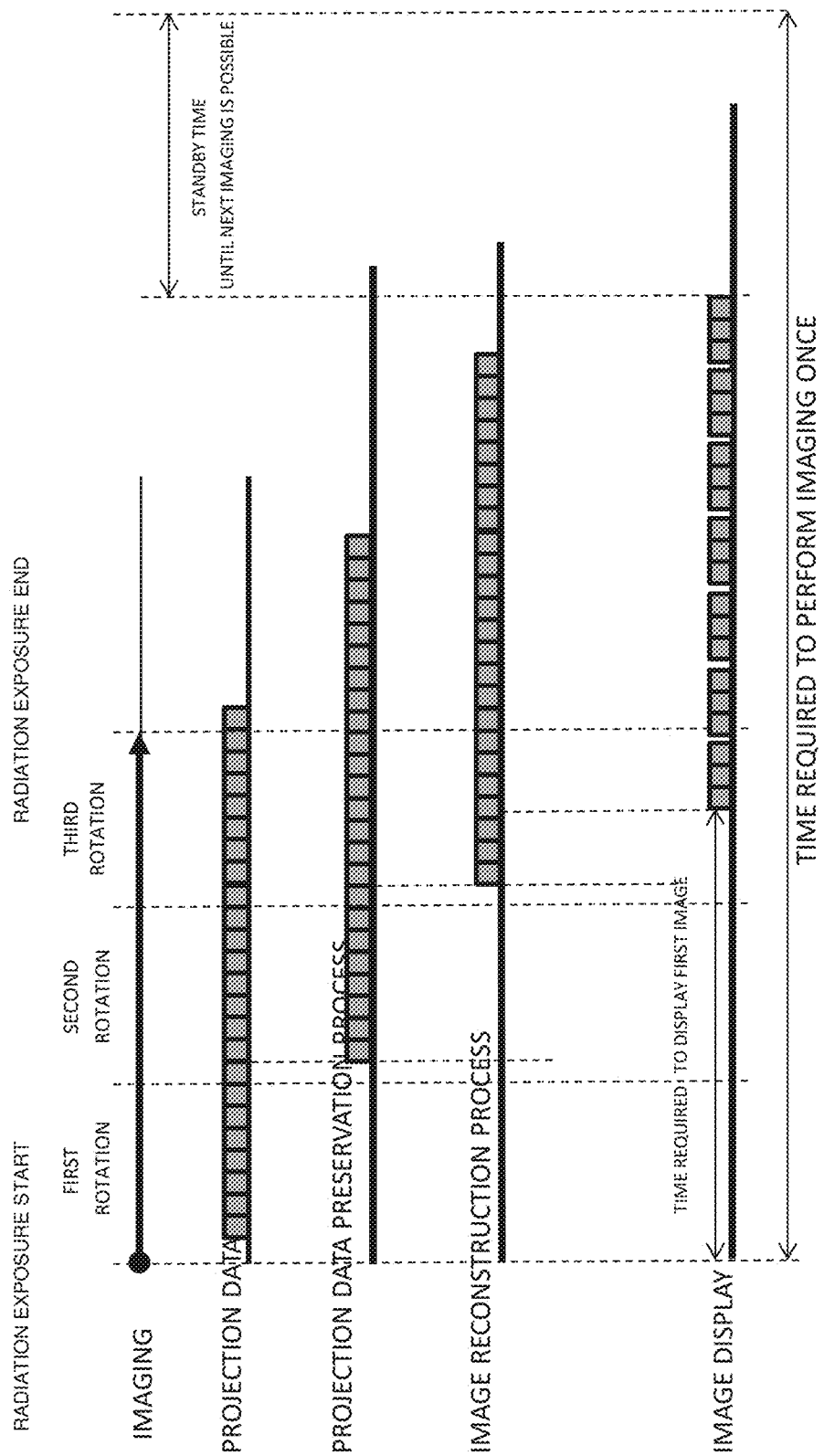
FIG. 6 is a timing chart related to display control in an X-ray CT device of the related art.

On the other hand, as illustrated in FIG. 6, in the related art, since display control is not performed, projection data is preserved after the projection data is generated, and then a reconstruction process and display of a reconstructed image are performed. Thus, since a time interval between displayed images is not necessarily constant, and the time to preserve projection data after an image is displayed is required to be secured, a standby time until the next imaging is performed is lengthened.

As mentioned above, in the X-ray CT device according to the present embodiment, a reconstruction process and a projection data preservation process are performed in parallel to an imaging process, and thus it is possible to reduce the time required to display a first image from starting of imaging. Control is performed such that only a reconstructed image created by using preserved projection data is displayed even though a reconstruction process and a preservation process which are sequentially performed are asynchronous, and thus it is possible to display sequentially generated reconstructed images at a uniform time interval and thus to improve operability. Preservation is also sequentially performed, and thus it is possible to reduce a standby time until the next imaging is started from finishing of imaging.

Therefore, in the X-ray CT device according to the present embodiment, in so-called CT examination, it is possible to efficiently perform a projection data preservation process and also to display an image in real time while performing consecutive imaging. Since the projection data preservation process is compound along with finishing of imaging, a user's standby time after an image is displayed is reduced, and thus the user can immediately perform the next imaging.

Second Embodiment

Next, a description will be made of an X-ray CT device according to a second embodiment of the present invention. In the first embodiment, a description has been made of an example in which the data preservation processing unit notifies the display control unit 212 of a projection data preservation situation as preservation information, and performs display control on the basis thereof. In the present embodiment, the data preservation processing unit notifies the display control unit 212 of an X-ray data preservation situation as preservation information, and performs display control on the basis thereof. The X-ray CT device according to the present embodiment has the same configuration as that of the X-ray CT device according to the first embodiment, and thus a detailed description of each constituent element will be omitted.

Figure 7:
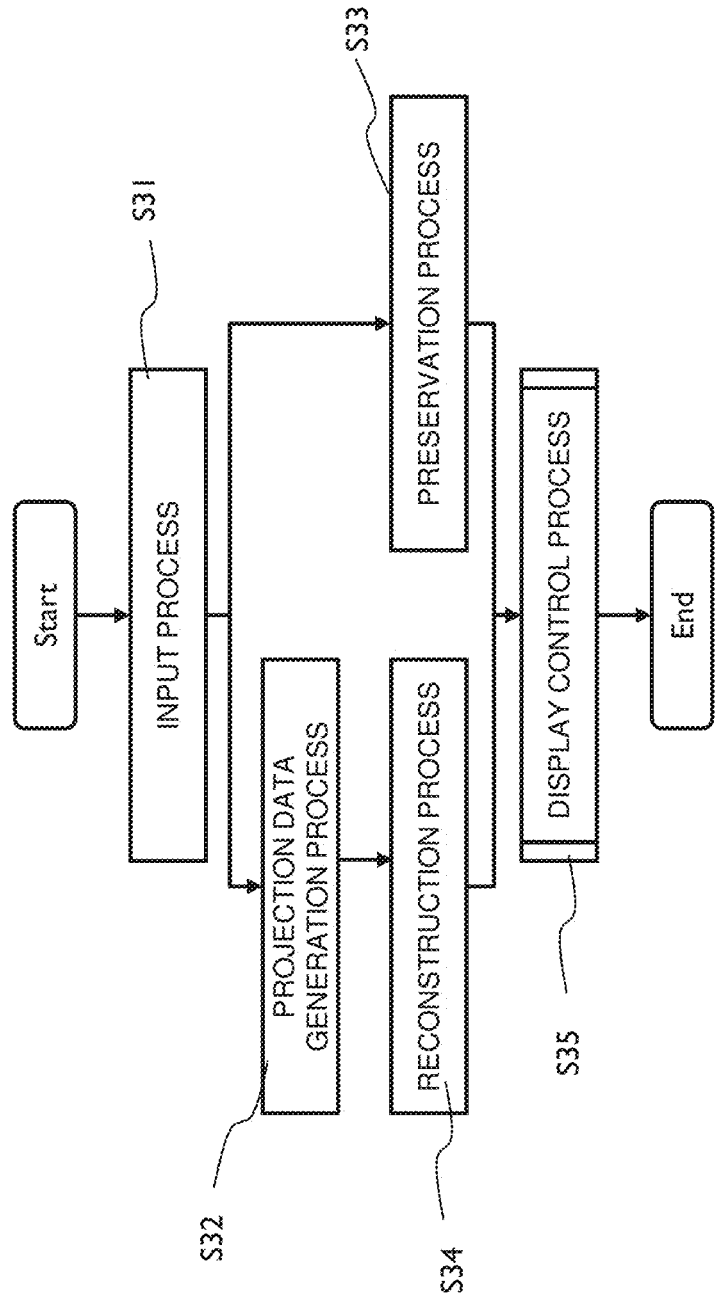
FIG. 7 is a flowchart illustrating a flow of a process in a display control unit of an X-ray CT device according to a second embodiment of the present invention.

In the X-ray CT device according to the present embodiment, with reference to a flowchart of FIG. 7, a description will be made of processes until a reconstructed image is generated from imaging.

Figure 8:
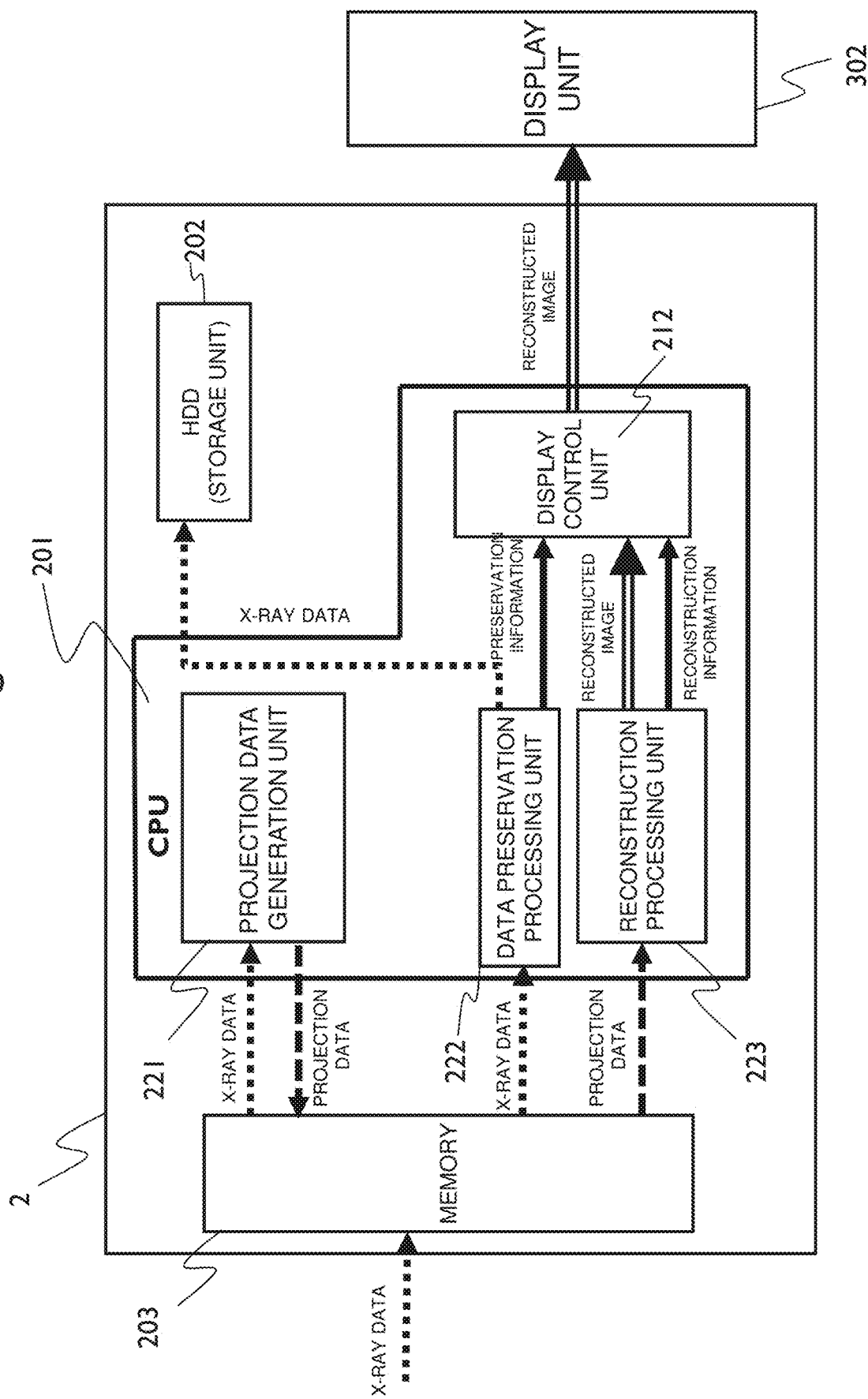
FIG. 8 is an explanatory diagram illustrating a flow of data until a reconstructed image is generated from imaging in the X-ray CT device according to the second embodiment of the present invention.

In step S31, a process of inputting X-ray data is performed. In other words, in a case where an imaging process is performed by the scanner 1, X-ray data collected in the scanner 1 is sequentially input to the memory 203 (refer to FIG. 8). In the subsequent step S32, the projection data generation unit 222 generates projection data on the basis of the X-ray data input to the memory 203. Specifically, as illustrated in FIG. 8, the projection data generation unit 221 reads the X-ray data stored in the memory 203, multiplies the X-ray data by a logarithmic conversion coefficient so as to obtain a logarithm, performs a calibration process so as to generate projection data, and stores the generated projection data into the memory 203.

In step S23, the data preservation processing unit 222 sequentially stores the X-ray data in the memory 203 stored in step S21 into the storage unit 202, and also generates preservation information which is then output to the display control unit 212. In other words, the X-ray data is preserved into the storage unit 202 in the unit of a predetermined data amount.

Here, the predetermined data amount according to the present embodiment is the minimum data amount of X-ray data required for the reconstruction processing unit 223 to start a reconstruction process. The data preservation processing unit 222 counts angle numbers of preserved X-ray data as the preservation information, holds the latest angle number ($E_c$), and notifies the display control unit of the angle number. The data preservation processing unit 222 updates the angle number ($E_c$) as the preservation information whenever the X-ray data preservation process is performed.

In step S24, the reconstruction processing unit 223 performs a reconstruction process on the projection data which is generated by the projection data generation unit 22 and is stored in the memory 203, in parallel to the process in step S23. In other words, the reconstruction processing unit 223 reads, from the memory 203, projection data at a plurality of angles required to perform a reconstruction process, that is, projection data which is convertible, and performs the reconstruction process thereon.

The same process is repeatedly performed, and thus a reconstructed image is created. As illustrated in FIG. 8, the reconstruction processing unit 223 sequentially outputs generated reconstructed images to the display control unit 212, and sequentially outputs image numbers of the generated reconstructed images to the display control unit 212 as reconstruction information.

The preservation process in step S33 and the reconstruction process in step S34 are performed in parallel to each other but are asynchronously performed. Thus, in step S25, the display control unit 212 controls only a reconstructed image created by using projection data generated on the basis of preserved X-ray data to be displayed, and sequentially displays reconstructed images on the display unit 302 at a uniform time interval.

Figure 9:
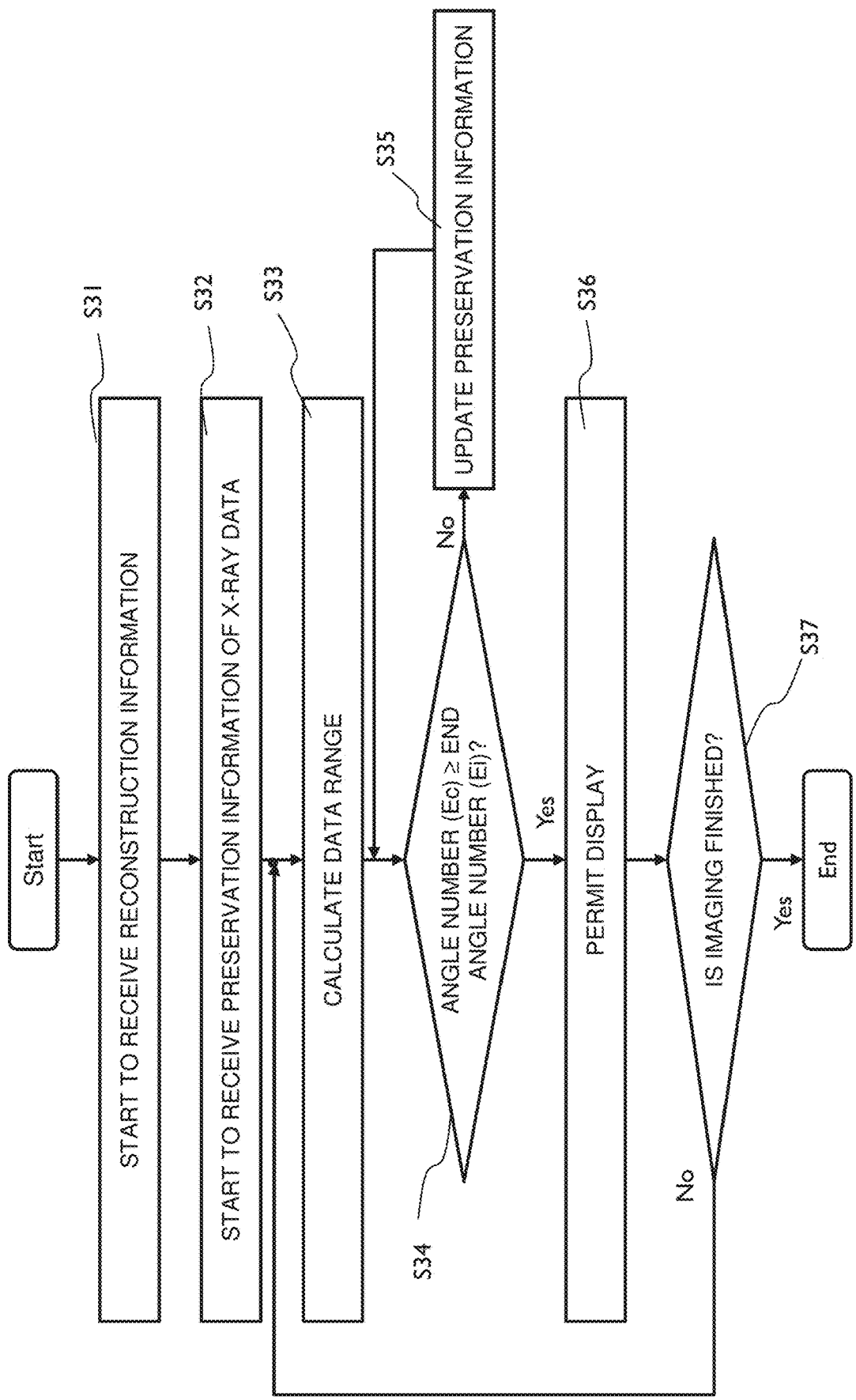
FIG. 9 is a flowchart illustrating a flow of a process in a display control unit of the X-ray CT device according to the second embodiment of the present invention.

Next, with reference to a flowchart of FIG. 9, a description will be made of details of a process in the display control unit 212.

In the X-ray CT device, in a case where imaging is started, and the control section 2 receives X-ray data from the scanner 1, and starts various processes, the display control unit 212 starts to receive reconstruction information from the reconstruction processing unit 223 in step S31. Ina case where the reconstruction information starts to be received, the display control unit 212 checks an image number (i) indicated by the reconstruction information.

Next, the display control unit 212 starts to receive preservation information from the data preservation processing unit 222 in step S32. In a case where the preservation information starts to be received, the display control unit 212 checks the latest angle number (Ec) of X-ray data stored in the storage unit 202 on the basis of the preservation information.

In step S33, the display control unit 212 calculates a start angle number ($S_i$) and an end angle number ($E_i$) of X-ray data which is a base of projection data from which the reconstructed image is generated by using the image number (i) checked in step S31. The start angle number and the end angle number are fundamentally calculated by using Equations (1) and (2) in the same manner as in the first embodiment, but, in the present embodiment, preservation information is information not based on projection data but based on X-ray data, and thus $T_f$, $T_h$, and $L_h$ in Equations (1) and (2) are modified in consideration of a process in an angular direction in generation of projection data.

For example, in a case where the projection data generation unit 221 down-samples two consecutive pieces of X-ray data in the angular direction into a single piece of X-ray data, each of $T_f$ and $T_h$ is modified to a value which is twice the value in the first embodiment, and then the start angle number ($S_i$) and the end angle number ($E_i$) corresponding to the image number (i) are calculated.

For example, in a case where the projection data generation unit 221 performs a convolution filtering process using three consecutive pieces of X-ray data in the angular direction, each of $T_f$ and $T_h$ is modified to a value obtained by adding 2 to the value in the first embodiment. $L_h$ is also modified by using modified $T_h$, and then the start angle number ($S_i$) and the end angle number ($E_i$) corresponding to the image number (i) are calculated.

In the next step S34, the angle number ($E_c$) related to the preservation information acquired from the data preservation processing unit 222 is compared with the end angle number ($E_i$) calculated in step S33 in terms of the magnitude. In a case where the preserved angle number is smaller than the end angle number, the image with the image number (i) is not permitted to be displayed, and the flow proceeds to step S25. In a case where the preservation information is updated, the flow returns to step S34, and the angle number ($E_c$) related to the preservation information is compared with the end angle number ($E_i$) calculated in step S33 in terms of the magnitude again.

In a case where the angle number is larger than or the same as the end angle number, the flow proceeds to step S36, the display control unit 212 permits the reconstructed image with the image number (i) to be displayed on the display unit 302, and the flow proceeds to step S37. In step S37, it is determined whether or not the overall imaging is finished, and, in a case where imaging is not finished, the flow returns to step S33, and the processes are repeatedly performed until imaging is finished. In a case where imaging is finished, the processes are finished.

As mentioned above, in the X-ray CT device according to the present embodiment, a reconstruction process and a X-ray data preservation process are performed in parallel to an imaging process, and thus it is possible to reduce the time required to display a first image from starting of imaging and also to reduce a standby time until the next imaging is started from finishing of imaging. Since X-ray data before generation of projection data is preserved, a reconstruction process can be performed by optimizing a parameter for a projection data generation process as necessary after imaging is finished, and thus it is possible to improve image quality.

Modification Example

In the first embodiment, a description has been made of an example of generating only one type of projection data, but a plurality of types of projection data may be generated. For example, in a case where energy information is included in X-ray data as in multi-energy imaging, projection data is generated for each energy band. In other words, in a case of multi-energy imaging, generation of projection data, a data preservation process, a reconstruction process, and the like are performed for each energy band.

Therefore, input X-ray data is divided into N pieces of X-ray data on the basis of energy information of an X-ray, and a process is performed on each piece of X-ray data. In the present modification example, an image combination unit which performs an image combination process on a reconstructed image generated for each energy band according to energy information of each image, and the image combination unit outputs a generated combined image to the display control unit 212. The display control unit 212 displays the generated combined image on the display unit 302 according to preservation information for each energy band and reconstruction information for each energy band.

REFERENCE SIGNS LIST 1 scanner
2 control section
3 input/output unit
100 gantry
101 bed
201 CPU
202 storage unit
203 memory
211 calculation unit
212 display control unit
221 projection data generation unit
222 data preservation processing unit
223 reconstruction processing unit
301 input unit
302 display unit

The invention claimed is:

1. An X-ray CT device comprising:
   a bed on which a subject is examined;
   a scanner that detects a dose of an X-ray which is applied from a periphery of the subject on the bed and is transmitted through the subject, and acquires X-ray data;
   a calculator that performs a predetermined calculation on the X-ray data acquired by the scanner to generate image data;
   a storage that preserves at least one of the X-ray data and the image data;
   a display that displays an image generated on a basis of the X-ray data; and
   a display controller that controls an image to be displayed on the display,
   wherein the calculator includes:
      a projection data generator that generates, as the image data, projection data on a basis of the X-ray data,
      a data preservation processor that preserves at least one of the X-ray data and the projection data in the storage unit in a unit of a predetermined data amount in parallel to an imaging process in the scanner, and also notifies the display controller of a preservation information indicating a progress situation of a preservation process whenever a preservation of the predetermined data amount is completed, and
   a reconstruction processor that performs a reconstruction process on the projection data in a unit of a predetermined data amount so as to generate a reconstructed image in parallel to an imaging process in the scanner, and also notifies the display controller of a reconstruction information indicating a progress situation of the reconstruction process whenever the reconstruction process is performed, and
   wherein the display controller controls a display timing of a reconstructed image to be displayed on the display on a basis of the preservation information and the reconstruction information.

2. The X-ray CT device according to claim 1,
   wherein the preservation information includes an angle number of projection data preserved last among pieces of the preserved projection data,
   wherein the reconstruction information includes an image number i, wherein i is a positive integer indicating a number of reconstructed images, and
   wherein the display controller calculates an angular range required to generate a reconstructed image related to the image number i, and controls a timing of the reconstructed image related to the image number i on a basis of the angular range and the angle number.

3. The X-ray CT device according to claim 2,
wherein the display controller calculates the angular range and the angle number by using a number of rotations, $R_i$, and a center angle number $T_i$, obtained according to following Equations (1) and (2):

$$R_i = (Z_0 - (Z_1 + Z_2) \pm (L_h + \lambda) + D \times (i-1)/L_R \quad (1)$$

$$T_i = \text{CEIL}((T_f + \tau) \times R_i - \delta) - (T_h + \tau/2) - 1 \quad (2)$$

where i indicates an image number, $R_i$ indicates a number of rotations, $T_i$ indicates a center angle number, $T_f$ indicates an angular range required to create a single image, $T_h$ indicates a half range of the angular range required to create a single image, $Z_0$ indicates a leading image position, $Z_1$ indicates a leading position of the bed, $Z_2$ indicates an offset value of a bed position, $L_h$ indicates a value of a bed movement amount into which $T_h$ is converted, D indicates an image interval, i indicates an image number, $L_R$ indicates a bed movement amount per rotation, $\delta$ indicates a value for adjusting round-up, $\lambda$ indicates a value of a bed movement amount into which $\tau/2$ is converted, $\tau$ indicates an extended range of an angular range changed depending on an algorithm for an inverse projection process and required to create a single image, and CEIL indicates a round-up function.

4. The X-ray CT device according to claim 1,
wherein the preservation information includes an angle number of X-ray data preserved last among pieces of the preserved X-ray data,
wherein the reconstruction information includes an image number i, wherein i is a positive integer indicating a number of reconstructed images, and
wherein the display controller calculates an angular range required to generate a reconstructed image related to the image number i, and controls a timing of the reconstructed image related to the image number i on a basis of the angular range and the angle number.

5. The X-ray CT device according to claim 4,
wherein the display controller calculates the angular range and the angle number by using a number of rotations, $R_i$, and a center angle number, $T_i$, obtained according to following Equations (1) and (2):

$$R_i = (Z_0 - (Z_1 + Z_2) \pm (L_h + \lambda) + D \times (i-1)/L_R \quad (1)$$

$$T_i = \text{CEIL}((T_f + \tau) \times R_i - \delta) - (T_h + \tau/2) - 1 \quad (2)$$

where i indicates an image number, $R_i$ indicates a number of rotations, $T_i$ indicates a center angle number, $T_f$ indicates an angular range required to create a single image, $T_h$ indicates a half range of the angular range required to create a single image, $Z_0$ indicates a leading image position, $Z_1$ indicates a leading position of the bed, $Z_2$ indicates an offset value of a bed position, $L_h$ indicates a value of a bed movement amount into which $T_h$ is converted, D indicates an image interval, i indicates an image number, $L_R$ indicates a bed movement amount per rotation, $\delta$ indicates a value for adjusting round-up, $\lambda$ indicates a value of a bed movement amount into which $\tau/2$ is converted, $\tau$ indicates an extended range of an angular range changed depending on an algorithm for an inverse projection process and required to create a single image, and CEIL indicates a round-up function.

6. The X-ray CT device according to claim 1,
wherein the reconstruction processor generates a multi-energy image, and
wherein the display controller displays the multi-energy image on the display on a basis of the preservation information and the reconstruction information.

7. An image display method comprising:
an imaging step of detecting a dose of an X-ray, which is applied from a periphery of a subject on a bed and is transmitted through the subject, and acquiring X-ray data;
a calculation step of performing a predetermined calculation on the X-ray data acquired by the imaging step to generate image data;
a storage step of preserving at least one of the X-ray data and the image data; and
a display step of displaying an image generated on a basis of the X-ray data on a display unit,
wherein the calculation step includes:
   a projection data generation step of generating, as the image data, projection data on a basis of the X-ray data,
   a data preservation processing step of preserving at least one of the X-ray data and the projection data in a unit of a predetermined data amount in parallel to an imaging process in the imaging step, and also performing a notification of preservation information indicating a progress situation of a preservation process whenever a preservation of the predetermined data amount is completed, and
   a reconstruction processing step of performing a reconstruction process on the projection data, in a unit of a predetermined data amount so as to generate a reconstructed image in parallel to an imaging process in the imaging step, and also performing a notification of reconstruction information indicating a progress situation of the reconstruction process whenever the reconstruction process is performed, and
wherein the display step further comprises controlling a display timing of a reconstructed image to be displayed on the display unit on a basis of the preservation information and the reconstruction information.

* * * * *